United States Patent
Kim et al.

(10) Patent No.: US 8,754,033 B2
(45) Date of Patent: Jun. 17, 2014

(54) PEPTIDES FOR INHIBITING TRANSGLUTAMINASE

(75) Inventors: Soo youl Kim, Seoul (KR); In hoo Kim, Goyang-si (KR); Sung soo Park, Busan (KR)

(73) Assignee: National Cancer Center, Gyeonggi-Do (KR)

( * ) Notice: Subject to any disclaimer, the term of this patent is extended or adjusted under 35 U.S.C. 154(b) by 705 days.

(21) Appl. No.: 11/918,340

(22) PCT Filed: Oct. 11, 2006

(86) PCT No.: PCT/KR2006/004089
§ 371 (c)(1),
(2), (4) Date: Apr. 10, 2008

(87) PCT Pub. No.: WO2007/069817
PCT Pub. Date: Jun. 21, 2007

(65) Prior Publication Data
US 2009/0197812 A1    Aug. 6, 2009

(30) Foreign Application Priority Data
Dec. 16, 2005 (KR) .................. 10-2005-0124420

(51) Int. Cl.
| A61K 38/00 | (2006.01) |
| C12Q 1/00 | (2006.01) |
| C12N 9/00 | (2006.01) |
| C12N 9/99 | (2006.01) |
| C12N 1/20 | (2006.01) |
| C12N 15/00 | (2006.01) |
| C07H 21/04 | (2006.01) |

(52) U.S. Cl.
USPC ............ 514/1.1; 435/4; 435/183; 435/184; 435/252.3; 435/320.1; 536/23.2

(58) Field of Classification Search
None
See application file for complete search history.

(56) References Cited

FOREIGN PATENT DOCUMENTS

| EP | 0632723 B1 | | 1/1995 |
| WO | WO 02/27031 | * | 4/2002 |
| WO | WO 03/012068 | * | 2/2003 |
| WO | 93/18760 A1 | | 9/2003 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Park, Sung-Soo, et al. "Transglutaminase 2 Mediates Polymer Formation of I-KBa through C-terminal Glutamine Cluster," The Journal of Biological Chemistry vol. 281, No. 46, pp. 34965-34972, Nov. 17, 2006.

Kim, Soo-Youl "Transglutaminase 2 in inflammation" Frontiers in Bioscience 11, p. 3026-3035, Sep. 1, 2006.
Antonyak, Marc A., et al. "Augmentation of Tissue Transglutaminase Expression and Activation by Epidermal Growth Factor Inhibit Doxorubicin-induced Apoptosis in Human Breast Cancer Cells" The Journal of Biological Chemistry, vol. 279, No. 40, Issue of Oct. I, pp. 41461-41467, 2004.
Kim, Dae-Seok, et al. "Reversal of Drug Resistance in Breast Cancer Cells by Transglutaminase 2 Inhibition and Nuclear Factor-kB Inactivation" Cancer Res 2006: 66(22): 10936-43.
Lee, Jongmin, et al., "Transglutaminase 2 Induces Nuclear Factor-KB Activation via a Novel Pathway in BV-2 Microglia" The Journal of Biological Chemistry, vol. 279, No. 51, Issue of Dec. 17, pp. 53725-53735, 2004.
Park, Key Chung, et al. "Transglutaminase 2 induces nitric oxide synthesis in BV-2 microglia" Biochemical and Biophysical Research Communications 323 (2004) 1055-1062.
Igarashi, Shuichi, et al. "Suppression of aggregate formation and apoptosis by transglutaminase inhibitors in cells expressing truncated DRPLA protein with an expanded polyglutamine stretch" Nature Genetics, vol. 18 Feb. 1998, p. 111-7.
Karpuj, Marcela V., et al. "Prolonged survival and decreased abnormal movements in transgenic model of Huntington disease, with administration of the transglutaminase inhibitor cystamine" Nature Medicine, vol. 8 • No. 2 • Feb. 2002, p. 143-9.
Sohn, Joonhong, et al. "Novel transglutaminase inhibitors reverse the inflammation of allergic conjunctivitis" J. Clin. Invest. 111:121-128 (2003).
Kim, Soo-Youl "New target aganist inflammatory diseases: transglutaminase 2" Arch Immunol Ther Exp, 2004, 52, 332-337.
Tergaonkar, Vinay , et al. "IKB Kinase-Independent IKBa Degradation Pathway: Functional NF-KB Activity and Implications for Cancer Therapy" Molecular and Cellular Biology, Nov. 2003, p. 8070-8083, vol. 23, No. 22.
Jung Mo Kim et al., "A New Regulatory Mechanism of NF-κB Activation by I-κBβ in Cancer Cells" J. Mol Biol 2008 384:756-765.
Jongmin Lee et al., "Transglutaminase 2 Induces Nuclear Factor-κB Activation via a Novel Pathway in BV-2 Microglia" The Journal of Biological Chemistry 2004 279(51):53725-53735.
Suh GY et al., "A Peptide with anti-transglutaminase activity decreases lipopolysaccharide-induced lung inflammation in mice." Exp Lung Res. Jan.-Feb. 2006; 32(1-2):43-53.
JP 2004-508003A English Translation of Abstract.
JP 2005-507650A English Translation of Abstract.

* cited by examiner

*Primary Examiner* — Christian Fronda
(74) *Attorney, Agent, or Firm* — Tanya A. Arenson; Casimir Jones, S.C.

(57) ABSTRACT

Disclosed herein are transglutaminase peptide inhibitors which have inhibitory activity against transglutaminase, and a pharmaceutical composition comprising one of them as an active ingredient. The inhibitors or the composition is useful in the prevention and treatment of various diseases caused by aberrant transglutaminase activation, including inflammatory diseases and cancers. Also, methods for treating various inflammatory diseases and cancers and for preparing mutant peptides capable of inhibiting transglutaminase are also disclosed.

2 Claims, 6 Drawing Sheets

FIG. 4

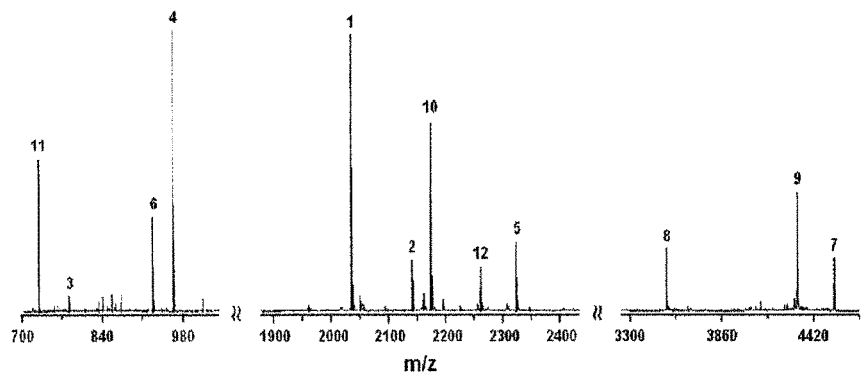

| SEQ ID NO | | Mass (MH⁺) | | Δmass | Expected Peptide | |
|---|---|---|---|---|---|---|
| | | Measured | Calculated | | | |
| 15 | 1 | 2033.91 | 2033.93 | −0.02 | 1 − 17 | MFQAAERPQEWAMEGPR |
| 16 | 2 | 2140.90 | 2140.92 | −0.02 | 30 − 47 | HDSGLDSMKDEEYEQMVK |
| 17 | 3 | 787.41 | 787.43 | −0.02 | 48 − 53 | ELQEIR |
| 18 | 4 | 967.50 | 967.52 | −0.02 | 54 − 61 | LEPQEVPR |
| 19 | 5 | 2323.14 | 2323.16 | −0.02 | 68 − 87 | QQLTEDGDSFLHLAIIHEEK |
| 20 | 6 | 932.50 | 932.52 | −0.02 | 88 − 95 | ALTMEVIR |
| 21 | 7 | 4544.19 | 4544.33 | −0.14 | 99 − 140 | GDLAFLNFQNNLQQTPLHLAVITNQPEIAEALLGAGCDPELR |
| 22 | 8 | 3528.57 | 3528.78 | −0.21 | 144 − 177 | GNTPLHLACEQGCLASVGVLTQSCTTPHLHSILK |
| 23 | 9 | 4319.93 | 4312.12 | −0.19 | 178 − 218 | ATNYNGHTCLHLASIHGYLGIVELLVSLGADVNAQEPCNGR |
| 24 | 10 | 2173.24 | 2173.26 | −0.02 | 219 − 238 | TALHLAVDLQNPDLVSLLLK |
| 25 | 11 | 734.31 | 734.33 | −0.02 | 239 − 245 | CGADVNR |
| 26 | 12 | 2260.10 | 2260.12 | −0.02 | 246 − 264 | VTYQGYSPYQLTWGRPSTR |

FIG. 5

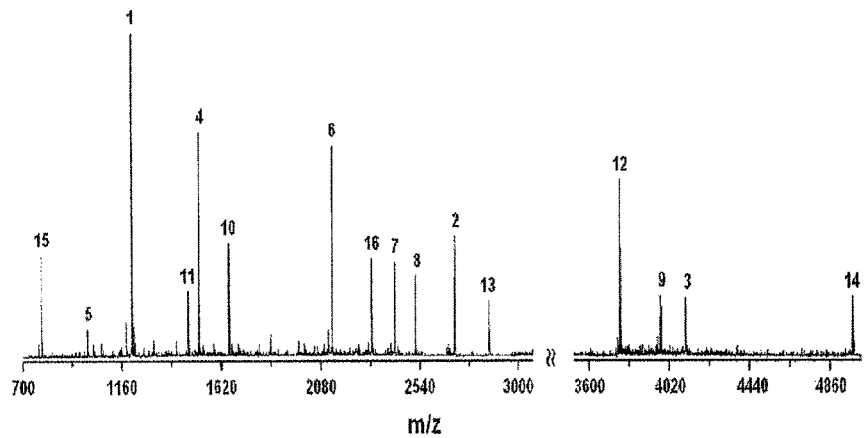

| SEQ ID NO | | Mass (MH+) | | Δmass | | Expected Peptide |
|---|---|---|---|---|---|---|
| | | Measured | Calculated | | | |
| 27 | 1 | 1206.56 | 1206.55 | 0.01 | 1 – 10 | MFQAAERPQE |
| 28 | 2 | 2704.27 | 2704.30 | -0.03 | 1 – 23 | MFQAAERPQEWAMEGPRDGLKKE |
| 29 | 3 | 4096.93 | 4096.97 | -0.04 | 1 – 35 | MFQAAERPQEWAMEGPRDGLKKERLLDDRHDSGLD |
| 30 | 4 | 1516.68 | 1516.75 | -0.07 | 11 – 23 | WAMEGPRDGLKKE |
| 31 | 5 | 999.54 | 999.56 | -0.02 | 15 – 23 | GPRDGLKKE |
| 32 | 6 | 2130.87 | 2130.98 | -0.11 | 24 – 41 | RLLDDRHDSGLDSMKDEE |
| 33 | 7 | 2422.96 | 2423.08 | -0.12 | 24 – 43 | RLLDDRHDSGLDSMKDEEYE |
| 34 | 8 | 2520.19 | 2520.32 | -0.13 | 52 – 72 | IRLEPQEVPRGSEPWKQQLTE |
| 35 | 9 | 3967.88 | 3968.03 | -0.15 | 52 – 85 | IRLEPQEVPRGSEPWKQQLTEDGDSFLHLAIIHE |
| 36 | 10 | 1654.78 | 1654.86 | -0.08 | 59 – 72 | VPRGSEPWKQQLTE |
| 37 | 11 | 1466.66 | 1466.72 | -0.06 | 73 – 85 | DGDSFLHLAIIHE |
| 38 | 12 | 3758.93 | 3759.04 | -0.11 | 93 – 125 | VIRQVKGDLAFLNFQNNLQQTPLHLAVITNQPE |
| 39 | 13 | 2863.34 | 2863.51 | -0.17 | 101 – 125 | LAFLNFQNNLQQTPLHLAVITNQPE |
| 40 41 | 14 | 4957.13 | 4957.49 | -0.36 | 154 – 200 | QGCLASVGVLTQSCTTPHLHSILKATNYNGHTCLHLASIHGY LGIVE |
| 42 | 15 | 787.43 | 787.46 | -0.03 | 210 – 208 | LLVSLGAD |
| 43 | 16 | 2316.86 | 2316.92 | -0.06 | 288 – 306 | SYDTESEFTEFTEDELPYD |

FIG. 6

```
MFQAAERPQE  WAMEGPRDGL  KKERLLDDRH  DSGLDSMKDE  EYEQMVKELQ
EIRLEPQEVP  RGSEPWKQQL  TEDGDSFLHL  AIIHEEKALT  MEVIRQVKGD
LAFLNFQNHL  QQTPLHLAVI  TNQPEIAEAL  LGAGCDPELR  DFRGNTPLHL
ACEQGCLASV  GVLTQSCTTP  HLHSILKATN  YNGHTCLHLA  SIHGYLGIVE
LLVSLGADVN  AQEPCNGRTA  LHLAVDLQNP  DLVSLLLKCG  ADVNRVTYQG
YSPYQLTWGR  PSTRIQQQLG  QLTLENLQML  PESEDEESYD  TESEFTEFTE
DELPYDDCVF  GGQRLTL
```

Red – Binding site with transglutaminase

FIG. 7

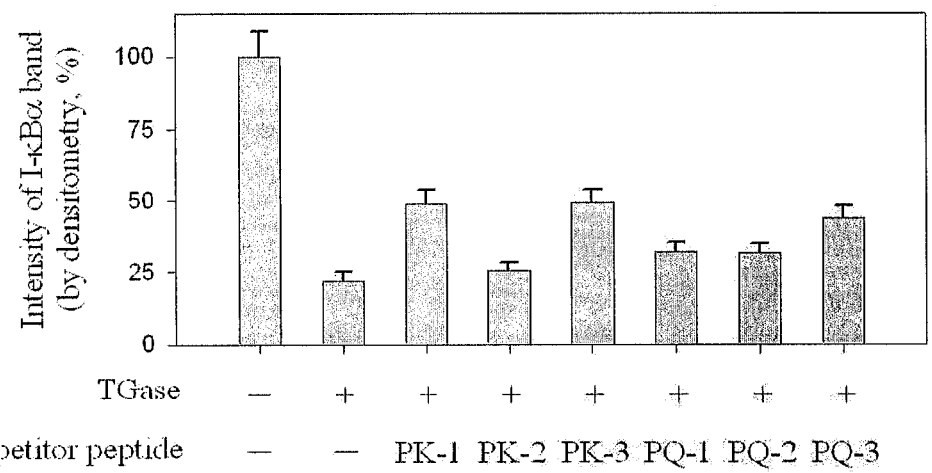

FIG. 8
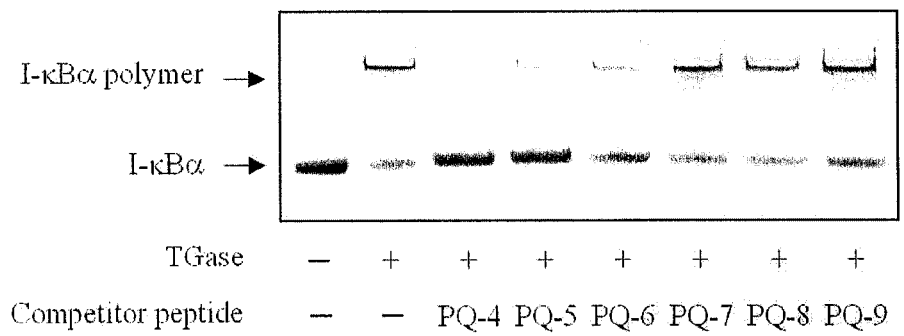
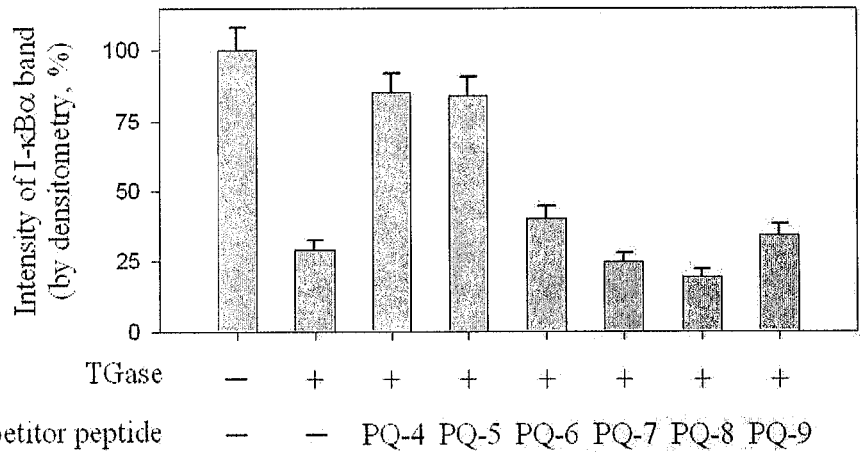
FIG. 9
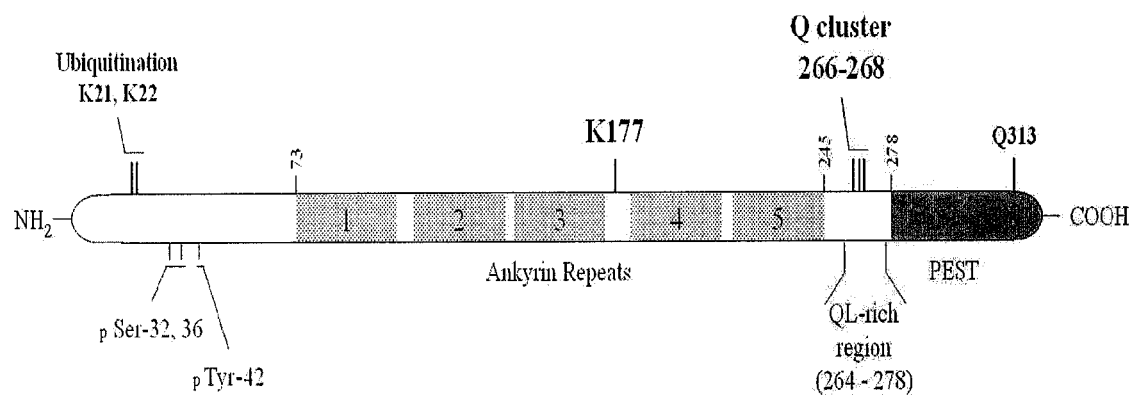

SEQUENCE LISTING

```
<160> NUMBER OF SEQ ID NOS: 43

<210> SEQ ID NO 1
<211> LENGTH: 317
<212> TYPE: PRT
<213> ORGANISM: Homo sapiens

<400> SEQUENCE: 1

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
            20                  25                  30

Gly Leu Asp Ser Met Lys Asp Glu Glu Tyr Glu Gln Met Val Lys Glu
        35                  40                  45

Leu Gln Glu Ile Arg Leu Glu Pro Gln Glu Val Pro Arg Gly Ser Glu
    50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125
```

```
Ala Leu Leu Gly Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Met Leu Pro Glu Ser Glu Asp Glu Glu Ser
        275                 280                 285

Tyr Asp Thr Glu Ser Glu Phe Thr Glu Phe Thr Glu Asp Glu Leu Pro
    290                 295                 300

Tyr Asp Asp Cys Val Phe Gly Gly Gln Arg Leu Thr Leu
305                 310                 315

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Arg Asp Gly Leu Lys Lys Glu Arg Leu Leu
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Ile His Glu Glu Lys Ala Leu Thr Met
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

His Ser Ile Leu Lys Ala Thr Asn Tyr
1               5

<210> SEQ ID NO 5
<211> LENGTH: 5
<212> TYPE: PRT
```

<213> ORGANISM: Artificial Sequence
<220> FEATURE:
<223> OTHER INFORMATION: Synthetic

<400> SEQUENCE: 5

Ile Leu Lys Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gly Val Leu Thr Gln Ser Cys Thr Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Glu Asn Leu Gln Met Leu Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Val Phe Gly Gly Gln Arg Leu Thr Leu
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic

<400> SEQUENCE: 9

Thr Arg Ile Gln Gln Gln Leu Gly Gln Leu Thr Leu
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Arg Ile Gln Gln Gln Leu Gly
1               5

<210> SEQ ID NO 11
<211> LENGTH: 5
<212> TYPE: PRT
<213> ORGANISM: Artificial Sequence
<220> FEATURE:

```
<223> OTHER INFORMATION: Synthetic

<400> SEQUENCE: 11

Leu Gly Gln Leu Thr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Arg Ile Gln Glu Glu Leu Gly
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Arg Ile Glu Gln Glu Leu Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Arg Ile Glu Glu Gln Leu Gly
1               5

<210> SEQ ID NO 15
<211> LENGTH: 17
<212> TYPE: PRT
<213> ORGANISM: Artificial Sequence
<220> FEATURE:
<223> OTHER INFORMATION: Synthetic

<400> SEQUENCE: 15

Met Phe Gln Ala Ala Glu Arg Pro Gln Glu Trp Ala Met Glu Gly Pro
1               5                   10                  15

Arg

<210> SEQ ID NO 16
<211> LENGTH: 18
<212> TYPE: PRT
<213> ORGANISM: Artificial Sequence
<220> FEATURE:
<223> OTHER INFORMATION: Synthetic

<400> SEQUENCE: 16

His Asp Ser Gly Leu Asp Ser Met Lys Asp Glu Glu Tyr Glu Gln Met
1               5                   10                  15

Val Lys

<210> SEQ ID NO 17
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 17

Glu Leu Gln Glu Ile Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Leu Glu Pro Gln Glu Val Pro Arg
1               5

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Gln Gln Leu Thr Glu Asp Gly Asp Ser Phe Leu His Leu Ala Ile Ile
1               5                   10                  15

His Glu Glu Lys
            20

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Ala Leu Thr Met Glu Val Ile Arg
1               5

<210> SEQ ID NO 21
<211> LENGTH: 42
<212> TYPE: PRT
<213> ORGANISM: Artificial Sequence
<220> FEATURE:
<223> OTHER INFORMATION: Synthetic

<400> SEQUENCE: 21

Gly Asp Leu Ala Phe Leu Asn Phe Gln Asn Asn Leu Gln Gln Thr Pro
1               5                   10                  15

Leu His Leu Ala Val Ile Thr Asn Gln Pro Glu Ile Ala Glu Ala Leu
            20                  25                  30

Leu Gly Ala Gly Cys Asp Pro Glu Leu Arg
        35                  40

<210> SEQ ID NO 22
<211> LENGTH: 34
<212> TYPE: PRT
<213> ORGANISM: Artificial Sequence
<220> FEATURE:
<223> OTHER INFORMATION: Synthetic

<400> SEQUENCE: 22
```

```
Gly Asn Thr Pro Leu His Leu Ala Cys Glu Gln Cys Leu Ala Ser
1               5                   10                  15

Val Gly Val Leu Thr Gln Ser Cys Thr Thr Pro His Leu His Ser Ile
                20                  25                  30

Leu Lys
```

<210> SEQ ID NO 23
<211> LENGTH: 41
<212> TYPE: PRT
<213> ORGANISM: Artificial Sequence
<220> FEATURE:
<223> OTHER INFORMATION: Synthetic

<400> SEQUENCE: 23

```
Ala Thr Asn Tyr Asn Gly His Thr Cys Leu His Leu Ala Ser Ile His
1               5                   10                  15

Gly Tyr Leu Gly Ile Val Glu Leu Leu Val Ser Leu Gly Ala Asp Val
                20                  25                  30

Asn Ala Gln Glu Pro Cys Asn Gly Arg
            35                  40
```

<210> SEQ ID NO 24
<211> LENGTH: 20
<212> TYPE: PRT
<213> ORGANISM: Artificial Sequence
<220> FEATURE:
<223> OTHER INFORMATION: Synthetic

<400> SEQUENCE: 24

```
Thr Ala Leu His Leu Ala Val Asp Leu Gln Asn Pro Asp Leu Val Ser
1               5                   10                  15

Leu Leu Leu Lys
            20
```

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

```
Cys Gly Ala Asp Val Asn Arg
1               5
```

<210> SEQ ID NO 26
<211> LENGTH: 19
<212> TYPE: PRT
<213> ORGANISM: Artificial Sequence
<220> FEATURE:
<223> OTHER INFORMATION: Synthetic

<400> SEQUENCE: 26

```
Val Thr Tyr Gln Gly Tyr Ser Pro Tyr Gln Leu Thr Trp Gly Arg Pro
1               5                   10                  15

Ser Thr Arg
```

<210> SEQ ID NO 27
<211> LENGTH: 10
<212> TYPE: PRT
<213> ORGANISM: Artificial Sequence
<220> FEATURE:
<223> OTHER INFORMATION: Synthetic

<400> SEQUENCE: 27

Met Phe Gln Ala Ala Glu Arg Pro Gln Glu
1               5                   10

<210> SEQ ID NO 28
<211> LENGTH: 23
<212> TYPE: PRT
<213> ORGANISM: Artificial Sequence
<220> FEATURE:
<223> OTHER INFORMATION: Synthetic

<400> SEQUENCE: 28

Met Phe Gln Ala Ala Glu Arg Pro Gln Glu Trp Ala Met Glu Gly Pro
1               5                   10                  15

Arg Asp Gly Leu Lys Lys Glu
            20

<210> SEQ ID NO 29
<211> LENGTH: 35
<212> TYPE: PRT
<213> ORGANISM: Artificial Sequence
<220> FEATURE:
<223> OTHER INFORMATION: Synthetic

<400> SEQUENCE: 29

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
            20                  25                  30

Gly Leu Asp
        35

<210> SEQ ID NO 30
<211> LENGTH: 13
<212> TYPE: PRT
<213> ORGANISM: Artificial Sequence
<220> FEATURE:
<223> OTHER INFORMATION: Synthetic

<400> SEQUENCE: 30

Trp Ala Met Glu Gly Pro Arg Asp Gly Leu Lys Lys Glu
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Gly Pro Arg Asp Gly Leu Lys Lys Glu
1               5

<210> SEQ ID NO 32
<211> LENGTH: 18
<212> TYPE: PRT
<213> ORGANISM: Artificial Sequence
<220> FEATURE:
<223> OTHER INFORMATION: Synthetic

<400> SEQUENCE: 32

Arg Leu Leu Asp Asp Arg His Asp Ser Gly Leu Asp Ser Met Lys Asp
1               5                   10                  15

Glu Glu

<210> SEQ ID NO 33
<211> LENGTH: 20
<212> TYPE: PRT
<213> ORGANISM: Artificial Sequence
<220> FEATURE:
<223> OTHER INFORMATION: Synthetic

<400> SEQUENCE: 33

Arg Leu Leu Asp Asp Arg His Asp Ser Gly Leu Asp Ser Met Lys Asp
1               5                   10                  15

Glu Glu Tyr Glu
            20

<210> SEQ ID NO 34
<211> LENGTH: 21
<212> TYPE: PRT
<213> ORGANISM: Artificial Sequence
<220> FEATURE:
<223> OTHER INFORMATION: Synthetic

<400> SEQUENCE: 34

Ile Arg Leu Glu Pro Gln Glu Val Pro Arg Gly Ser Glu Pro Trp Lys
1               5                   10                  15

Gln Gln Leu Thr Glu
            20

<210> SEQ ID NO 35
<211> LENGTH: 34
<212> TYPE: PRT
<213> ORGANISM: Artificial Sequence
<220> FEATURE:
<223> OTHER INFORMATION: Synthetic

<400> SEQUENCE: 35

Ile Arg Leu Glu Pro Gln Glu Val Pro Arg Gly Ser Glu Pro Trp Lys
1               5                   10                  15

Gln Gln Leu Thr Glu Asp Gly Asp Ser Phe Leu His Leu Ala Ile Ile
            20                  25                  30

His Glu

<210> SEQ ID NO 36
<211> LENGTH: 14
<212> TYPE: PRT
<213> ORGANISM: Artificial Sequence
<220> FEATURE:
<223> OTHER INFORMATION: Synthetic

<400> SEQUENCE: 36

Val Pro Arg Gly Ser Glu Pro Trp Lys Gln Gln Leu Thr Glu
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic

<400> SEQUENCE: 37

Asp Gly Asp Ser Phe Leu His Leu Ala Ile Ile His Glu
1               5                   10

<210> SEQ ID NO 38
<211> LENGTH: 33
<212> TYPE: PRT

<213> ORGANISM: Artificial Sequence
<220> FEATURE:
<223> OTHER INFORMATION: Synthetic

<400> SEQUENCE: 38

Val Ile Arg Gln Val Lys Gly Asp Leu Ala Phe Leu Asn Phe Gln Asn
1               5                   10                  15
Asn Leu Gln Gln Thr Pro Leu His Leu Ala Val Ile Thr Asn Gln Pro
            20                  25                  30
Glu

<210> SEQ ID NO 39
<211> LENGTH: 25
<212> TYPE: PRT
<213> ORGANISM: Artificial Sequence
<220> FEATURE:
<223> OTHER INFORMATION: Synthetic

<400> SEQUENCE: 39

Leu Ala Phe Leu Asn Phe Gln Asn Asn Leu Gln Gln Thr Pro Leu His
1               5                   10                  15
Leu Ala Val Ile Thr Asn Gln Pro Glu
            20                  25

<210> SEQ ID NO 40
<211> LENGTH: 42
<212> TYPE: PRT
<213> ORGANISM: Artificial Sequence
<220> FEATURE:
<223> OTHER INFORMATION: Synthetic

<400> SEQUENCE: 40

Gln Gly Cys Leu Ala Ser Val Gly Val Leu Thr Gln Ser Cys Thr Thr
1               5                   10                  15
Pro His Leu His Ser Ile Leu Lys Ala Thr Asn Tyr Asn Gly His Thr
            20                  25                  30
Cys Leu His Leu Ala Ser Ile His Gly Tyr
            35                  40

<210> SEQ ID NO 41
<211> LENGTH: 5
<212> TYPE: PRT
<213> ORGANISM: Artificial Sequence
<220> FEATURE:
<223> OTHER INFORMATION: Synthetic

<400> SEQUENCE: 41

Leu Gly Ile Val Glu
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Leu Leu Val Ser Leu Gly Ala Asp
1               5

<210> SEQ ID NO 43
<211> LENGTH: 19
<212> TYPE: PRT
<213> ORGANISM: Artificial Sequence -continued

```
<220> FEATURE:
<223> OTHER INFORMATION: Synthetic

<400> SEQUENCE: 43

Ser Tyr Asp Thr Glu Ser Glu Phe Thr Glu Phe Thr Glu Asp Glu Leu
1               5                   10                  15

Pro Tyr Asp
```

PEPTIDES FOR INHIBITING TRANSGLUTAMINASE

TECHNICAL FIELD

The present invention relates to transglutaminase peptide inhibitors. More particularly, the present invention relates to transglutaminase-specific peptide inhibitors which inhibit transglutaminase-mediated I-κBα polymerization, thus being effective in the prevention and treatment of the diseases caused by transglutaminase activation. Also, the present invention is concerned with a pharmaceutical composition comprising one or more of the transglutaminase peptide inhibitors as an active ingredient and with a method for preventing or treating the diseases caused by transglutaminase activation, using the same.

BACKGROUND ART

Transglutaminases are protective enzymes which are responsible for blood clotting in response to tissue injury under normal conditions. However, these enzymes are also reported to play a crucial role in the pathological mechanism of various diseases in the absence of regulatory control of the level of expression thereof (Soo-Youl Kim: New Target Against Inflammatory Diseases: Transglutaminase 2. *Archivum Immunologiae & Therapiae Experimentalis* 52, 332-337, 2004. Soo-Youl Kim. Transglutaminase 2 in inflammation. *Front Biosci.* 11, 3026-3035, 2006). The expression of transglutaminases increases particularly upon the occurrence of various inflammatory diseases, including rheumatoid arthritis, diabetes, inflammatory myositis, atherosclerosis, stroke, liver cirrhosis, breast cancer, Alzheimer's disease, Parkinson's disease, Huntington's disease, encephalitis, celiac disease, etc. Also, transglutaminases are observed to increase in expression level, along with NF-κB, when cancer enters metastasis or changes into chemo-resistance or radio-resistance (Soo-Youl Kim. Transglutaminase 2 in inflammation. *Front Biosci.* 11, 3026-3035, 2006).

The relationship between transglutaminases and chemoresistance in cancer has remained unclear thus far. However, when the expression of transglutaminases was suppressed in chemoresistant breast cancer cells, the cancer cells were getting highly susceptible to chemicals, and finally died (Antonyak et al., Augmentation of tissue transglutaminase expression and activation by epidermal growth factor inhibit doxorubicin-induced apoptosis in human breast cancer cells. J Biol Chem. 2004 Oct. 1;279(40):41461-7.; Dae-Seok Kim et al. Reversal of Drug Resistance in Breast Cancer Cells by Transglutaminase 2 Inhibition and NF-κB Inactivation. Cancer Res. 2006. 66, 10936-10943).

Also, there is a strong reason for suppressing the activity of transglutaminases as the etiological mechanism for which the activation of transglutaminases is responsible is elucidated at the molecular level (Key Chung Park, Kyung Cheon Chung, Yoon-Seong Kim, Jongmin Lee, Tong H. Joh, and Soo-Youl Kim. Transglutaminase 2 induces nitric oxide synthesis in BV-2 microglia. *Biochem. Biophys. Res. Commun.* 323, 1055-1062, 2004; Jongmin Lee, Yoon-Seong Kim, Dong-Hee Choi, Moon S. Bang, Tay R. Han, Tong H. Joh, and Soo-Youl Kim. Transglutaminase 2 induces NF-KB activation via a novel pathway in BV-2 microglia. *J. Biol. Chem.* 279, 53725-53735, 2004; Dae-Seok Kim et al. Reversal of Drug Resistance in Breast Cancer Cells by Transglutaminase 2 Inhibition and Nuclear Factor-KB Inactivation. Cancer Res. 2006. Cancer Res. 2006. 66, 10936-10943).

Inflammation is largely attributable to NF-κB activation. NF-κB is known to be activated by kinases in signal transduction pathways. However, NF-κB was also found to be activated independently of kinases, thereby negating the function of kinase inhibitors (Tergaonkar et al., I-kappaB kinase-independent I-κBα degradation pathway: functional NF-kappaB activity and implications for cancer therapy. Mol Cell Biol. 2003 Nov;23(22):8070-83.).

In a previous study conducted by the present inventors, it was reported that transglutaminase activates NF-κB independently of the activation of kinases (IKK, NAK), by inducing crosslinking I-κBα (Jongmin Lee, et al. Transglutaminase 2 induces NF-κB activation via a novel pathway in BV-2 microglia. J. Biol. Chem. 279, 53725-53735, 2004). Transglutaminases are calcium-dependent enzymes, which can activate NF-κB only at an elevated intracellular level of calcium.

Upon inflammation, the activation of the transcriptional factor NF-κB leads to an increase in the expression not only of inflammatory factors including transglutaminases, but also of its inhibitor I-κBα. Continuous NF-κB activation is inhibited by I-κBα under normal conditions, but continues in chronic inflammatory diseases. Interestingly, TNF-α or LPS (lipopolysaccharide)-induced NF-κB activation gives rise to transglutaminase expression. Thus, aberrantly activated transglutaminases in inflammatory cells are expected to activate NF-κB directly or to further maintain activated NF-κB, thereby playing a key role in inflammation maintenance (FIG. 1). In addition, this vicious cycle may be a main cause of cancer metastasis and chemo-resistance (Jongmin Lee, et al. Transglutaminase 2 induces NF-kB activation via a novel pathway in BV-2 microglia. J. Biol. Chem. 279, 53725-53735, 2004).

Therefore, a transglutaminase inhibitor may play a crucial role in breaking the continuous cycle of NF-κB, on which the steroid-substituting effect proposed by the present inventors is based (Sohn, J., Kim, T. I., Yoon, Y. H., and Kim, S. Y.: Transglutaminase Inhibitor: A New Anti-Inflammatory Approach in Allergic Conjunctivitis. J. Clin. Invest. 111, 121-8, 2003).

Amine compounds are known to inhibit transglutaminase activity. Representative of the TGase inhibitors are cystamine (Nature Genetics 18, 111-117, 1998; Nature Medicine 8, 143-149, 2002) and putrescine. In addition to the amine compounds, other chemical inhibitors, such as monodansylcadaverine (J. Med. Chem. 15, 674-675, 1972), w-dibenzylaminoalkylamine (J. Med. Chem. 18, 278-284, 1975), 3-halo-4, 5-dihydroisoxazole (Mol. Pharmacol. 35, 701-706, 1989), and 2-[(2-oxopropyl)thio]imidazolium derivatives (Blood, 75, 1455-1459, 1990), were developed, but are reported to be so toxic as to non-specifically inhibit other enzymes in vivo.

Therefore, there is a need for safe and effective transglutaminase-specific inhibitors. Recently, Sohn et al. have succeeded in obtaining the same effect from recombinant peptides as steroidal drugs for the inflammation of allergic conjunctivitis to ragweed in a guinea pig model (Sohn, J., Kim, T. -I., Yoon, Y. -H., and Kim, S. -Y.: Transglutaminase Inhibitor: A New Anti-Inflammatory Approach in Allergic Conjunctivitis. J. Clin. Invest. 111, 121-8, 2003). In this regard, anti-flammin protein (PLA$_2$ inhibitor)- or elafin protein (very strong transglutaminase substrate, Nara, K., et al. 1994. Elastase inhibitor elafin is a new type of proteinase inhibitor which has a transglutaminase-mediated anchoring sequence termed "cementoin". J Biochem (Tokyo). 115:441-448)-derived synthetic peptides which mimic the catalytic site of transglutaminase were used.

Leading to the present invention, intensive and thorough research based on the foregoing, conducted by the present inventors, allows the present inventors to identify the positions of the glutamine and lysine residues involved in the transglutaminase-induced I-κBα polymerization, and find that I-κBα-derived peptides or homologs thereof containing these residues inhibit transglutaminase-induced I-κBα polymerization, thus acting as transglutaminase inhibitors.

DISCLOSURE OF THE INVENTION

It is therefore an object of the present invention to provide a peptide for inhibiting transglutaminase, comprising an I-κBα-derived fragment or a mutant thereof.

It is another object of the present invention to provide a composition for inhibiting transglutaminase, comprising the peptide as an active ingredient.

It is a further object of the present invention to provide a method for inhibiting transglutaminase, comprising the administration of the peptide.

It is still a further object of the present invention to provide a method for preparing a mutant of the peptide, which has inhibitory activity against transglutaminase-mediated I-κBα polymerization, comprising substituting, deleting, or inserting at least one amino acid residue of the amino acid sequence of the peptide.

BRIEF DESCRIPTION OF THE DRAWINGS

The above and other objects, features and advantages of the present invention will be more clearly understood from the following detailed description taken in conjunction with the accompanying drawings, in which:

FIGS. 4 and 5 shows MS analyses of peptides released from proteolytic digestion of I-κBα after transglutaminase-induced crosslinking thereof, wherein peptide masses are determined using MALDI-TOF;

FIG. 6 shows an amino acid sequence of I-κBα wherein red characters indicate a binding site to transglutaminase;

FIGS. 7 and 8 show transglutaminase-mediated I-κBα polymerization, rescued by treatment with the synthetic peptides; and FIG. 9 is a schematic diagram representing various functional domains and amino acid residues in I-κBα. In the N-terminal region of I-κBα are found two ubiquitination sites, two serine phosphorylation sites, and a tyrosin phosphorylation site. The C-terminal region contains PEST sequences and a QL(glutamine and leucine)-rich region. The five ankyrin repeats are represented by hatched boxes and the cross-linking sites are indicated above the map by bold characters.

BEST MODE FOR CARRYING OUT THE INVENTION

In accordance with an aspect, the present invention pertains to an I-κBα-derived peptide which inhibits transglutaminase activity.

Figure 1:
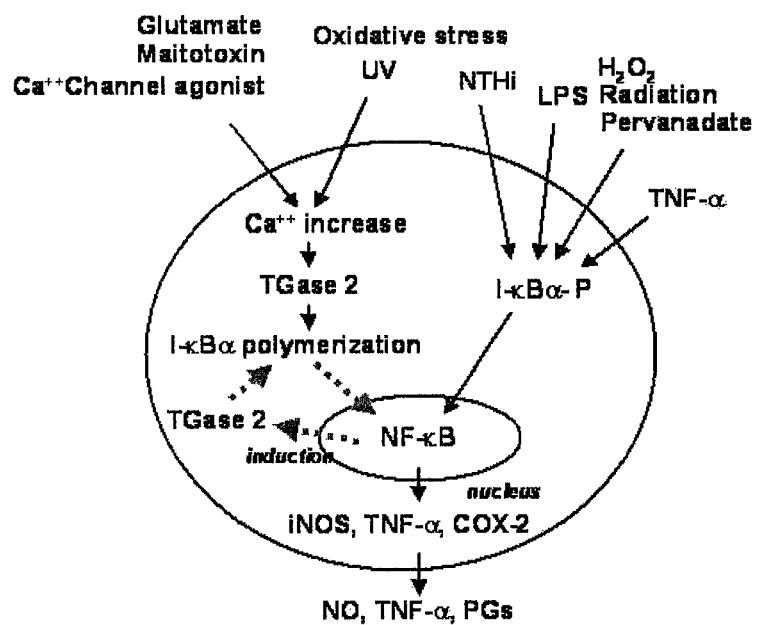
FIG. 1 is a schematic diagram illustrating the role of transglutaminase during the activation of immune cells (NTHi, nontypeable *Haemophilus influenza*; TLR, toll-like receptor; TNER, tumor necrosis factor-a receptor; IKK, I-κB kinase; CKII, casein kinase II; TK, tyrosine kinase; COX-2, cyclooxygenase-2; $PLA_2$, soluble phospholipase $A_2$; NO, nitric oxide)
Figure 2:
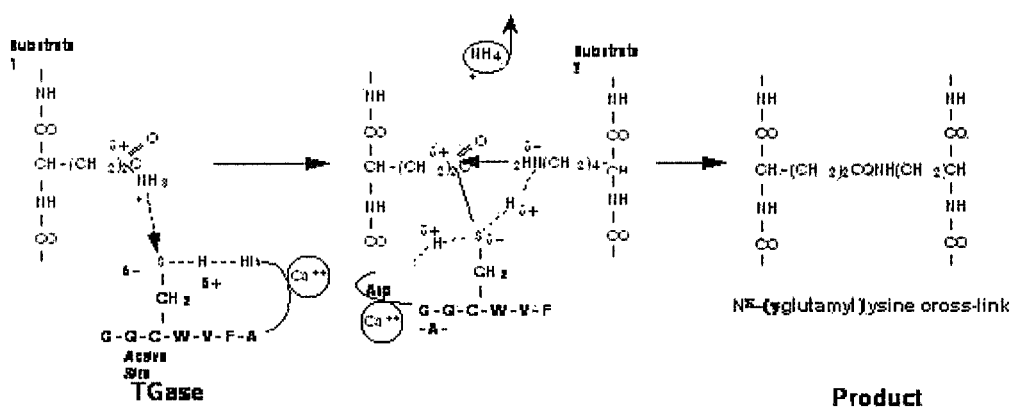
FIG. 2 is a sequence of enzymatic reactions of transglutaminase, wherein substrate 2 provides a lysine residue (acyl acceptor, amine donor) for [$N^\epsilon$-(γ-glutamyl)-L-lysine (GGEL)] isopeptide covalent bond formation with a glutamine residue, and GQCWVFA is the amino acid sequence located in the active site of transglutaminase. A thioester covalent enzyme intermediate is seen in the middle. This enzymatic reaction, based on a "ping-pong" kinetic mechanism, may utilize an amine compound (amines, diamines, polyamines), as an acyl receptor, instead of lysine residue.

Transglutaminase (TGase) belongs to a family of Ca2+-dependent enzymes that catalyze $N^\epsilon$-(γ-L-glutamyl)-L-lysine isopeptide bond formation between peptide bound lysine and glutamine residues (FIG. 2). $N^\epsilon$-(γ-L-glutamyl)-L-lysine cross-linking is known to stabilize intra- and extracellular proteins that are used for barrier functions in epithelia, apoptosis, and extracellular matrix formation. TGase is normally expressed at low levels in many different tissues and is inappropriately activated in a variety of pathological conditions. Particularly, inflammatory diseases and cancer give rise to an increase in TGase expression. In a previous study conducted by the present inventors, it was demonstrated that the mechanism by which TGase induces immune responses is based on the ability of transglutaminase to induce I-κBα polymerization, thereby activating NF-κB (Jongmin Lee, et al. Transglutaminase 2 induces NF-kB activation via a novel pathway in BV-2 microglia. *J. Biol. Chem.* 279, 53725-53735, 2004). According to the present invention, transglutaminase-specific peptide inhibitors are provided for inhibiting the polymerization of I-κBα in the transglutaminase activation mechanism (Park S. -S., et al. Transglutaminase 2 mediates polymer formation of I-kappa Balpha through C-terminal glutamine cluster. J Biol Chem. 2006 Sep. 20; [Epub ahead of print].).

The term "peptide", as used herein, means a polymer of amino acids joined together via an amide bond (or peptide bond). The peptides according to the present invention are transglutaminase-specific inhibitors which inhibit transglutaminase-induced I-κBα polymerization.

In greater detail, the peptides of the present invention, acting as transglutaminase inhibitors, are derived from an amino acid sequence of SEQ ID NO.: 1 for I-κBα, and specified as (i) a peptide fragment consisting of 5 or more consecutive amino acids of amino acid positions 11 to 30, with lysine 21 and lysine 22 contained therein, (ii) a peptide fragment consisting of 5 or more consecutive amino acids of amino acid positions 81 to 100, with lysine 87 contained therein, (iii) a peptide fragment consisting of 5 or more consecutive amino acids of amino acid positions 151 to 200, with lysine 177 contained therein, (iv) a peptide fragment consisting of 5 or more consecutive amino acids of amino acid positions 261 to 290, with glutamine 266 to 268 or glutamine 271 contained therein, or (v) a peptide fragment consisting of 5 or more consecutive amino acids of amino acid positions 301 to 317, with glutamine 313 contained therein (Park S. -S., et al. Transglutaminase 2 mediates polymer formation of I-κBα through C-terminal glutamine cluster. J Biol Chem. 2006, 281, 34965-72).

In an embodiment of the present invention, separate I-κBα is induced into polymerization in the presence of transglutaminase in order to determine the I-κBα site at which the transglutaminase-induced polymerization occurs. The I-κBα polymer is digested to completion with proteinase and the peptide digests are analyzed using a MALDI-TOF mass spectrometer (4700 Proteomics Analyzer, Applied Biosystems). Data on the MALDI-TOF mass spectrometer reveal that lysine residues at positions 21, 22, 87 and 177 and glutamine residues at positions 266-268, 271 and 313 are preferably used in transglutaminase-mediated cross-linking of I-κBα.

From the information on the amino acid residues involved in the transglutaminase-mediated I-κBα polymerization, one skilled in the art can readily synthesize various peptides which contain the polymerization-induced residues so as to exhibit inhibitory activity against transglutaminases (Park S. -S., et al. Transglutaminase 2 mediates polymer formation of I-kappa Balpha through C-terminal glutamine cluster. (J Biol Chem. 2006, 281, 34965-72).

In another embodiment of the present invention, peptides are synthesized on the basis of the lysine and glutamine residues to have amino acid sequences, RDGLKKERLL of SEQ ID NO.: 2, IHEEKALTM of SEQ ID NO.: 3, HSILKATNY of SEQ ID NO.: 4, ILKAT of SEQ ID NO.: 5, GVLTQSCTT of SEQ ID NO.: 6, ENLQMLP of SEQ ID NO.: 7, VFGGQRLTL of SEQ ID NO.: 8, TRIQQQLGQLTL of SEQ ID NO.: 9, RIQQQLG of 10, and LGQLT of SEQ ID NO.: 11, and found to inhibit transglutaminase-mediated I-κBα polymerization.

Further, mutants of the peptides according to the present invention fall within the scope of the present invention. As used herein, the term "mutants" mean peptides having amino acid sequences which differ from natural ones derived from I-κBα amino acid sequence due to deletion, insertion or non-conservative or conservative substitution of at least one amino acid residue or combinations thereof.

In a further embodiment of the present invention, mutants having the sequences RIQEELG of SEQ ID NO.: 12, RIEQELG of SEQ ID NO.: 13, and RIEEQLG of SEQ ID NO.: 14 are found to inhibit transglutaminase-mediated I-κBα polymerization.

The peptides of the present invention may have L-configuration or D-configuration or may be racemates thereof. Further, the peptides of the present invention may be modified according to purpose, such as derivatives having hydroxyl and/or methyl substituents on specific atoms or atom groups, an amide or an ester group substituted for a C-terminal carboxyl group, or hydrogen substituted for the N-terminal amino group.

In addition, the peptides of the present invention may comprise targeting signals, tags, labeled residues, or additional amino acid sequences adapted for increasing the stability thereof. A cell permeable peptide which promotes the introduction of the peptides into cells may also be added.

The peptides of the present invention can be prepared according to various techniques well known in the art, including chemical synthesis, cell-free protein synthesis, or genetic recombination.

Salts are possible forms of the peptides of the present invention. The peptides of the present invention may form salts with acids, such as inorganic acids (hydrochloric acid, hydrobromic acid, phosphoric acid, nitric acid or sulfuric acid), organic carboxylic acids (acetic acid, halo acetic acid such as trifluoroacetic acid, propionic acid, maleic acid, succinic acid, malic acid, citric acid, tartaric acid, or salicylic acid), and organic sulfonic acids (methane sulfonic acid or p-toluene sulfonic acid) containing sugar acid (glucuronic acid, galacturonic acid, gluconic acid, or ascorbic acid), acidic polysaccharide (hyaluronic acid, chondroitin sulfate, or arginic acid) or sulfonic acid ester (chondroitin sulfate).

In accordance with the present invention, the transglutaminase peptide inhibitors are effective in the prevention or treatment of all diseases that are caused as transglutaminases are inappropriately activated. Preferably, the peptides of the present invention can be used for the prophylaxis or treatment of inflammatory diseases or cancers which are caused by inappropriate transglutaminase activation.

In accordance with another aspect, the present invention pertains to a transglutaminase-inhibiting composition comprising at least one of the peptides of the present invention.

The term "inflammatory disease" means any disease or disorder is caused by the defense or inflammatory response of the body to injurious effects of a body state(physical, chemical and biological state) concomitant with erythema, edema, tenderness, heat and/or dysfunction syndromes. The composition of the present invention is useful in the prophylaxis and treatment of all inflammatory diseases that are induced by transglutaminase overexpression. Examples of the inflammatory diseases caused by transglutaminase activation include degenerative arthritis (rheumatoid arthritis), diabetes, autoimmune myositis (inflammatory myositis), artherosclerosis, strokes, hepatocirrhosis, breast cancer, Alzheimer's disease, Parkinson's disease, Huntington's disease, encephalitis and celiac disease.

As for cancers, these are found to significantly increase in the level of expression of transglutaminase upon metastasis or entry into chemo- or radio-resistance. Thus, the suppression of transglutaminase arises as a key in the prophylaxis and treatment of cancers as well as inflammatory disease. Concrete examples of the cancers for the treatment and prophylaxis of which the transglutaminase peptide inhibitors of the present invention can be applied include large intestinal cancer, small intestinal cancer, rectal cancer, anal cancer, esophageal cancer, pancreatic cancer, stomach caner, kidney cancer, uterine cancer, breast cancer, lung cancer, lymphoma, thyroid cancer, prostatic carcinoma, leukemia, skin cancer, colon cancer, encephaloma, bladder cancer, ovarian cancer, gallbladder carcinoma, etc, but are not limited thereto.

The term "prevention" or "prophylaxis" as used herein means all of the actions in which the occurrence of any disease caused by the activation of transglutaminase is restrained or retarded by the administration of the composition of the present invention. The term "treatment" as used herein means all of the actions in which any disease caused by the activation of transglutaminase has taken a turn for the better or been modified favorably by the administration of the composition of the present invention.

The composition of the present invention can be applied to mammals that may suffer from inflammatory diseases or cancers due to the activation of transglutaminase, including cattle, horses, sheep, pigs, goats, camels, antelopes, dogs, and cats, as well as humans.

The composition comprising at least one of the peptides of the present invention may be used alone or in combination with other compounds, such as sugar chains, lipids, nucleic acids, other peptides or proteins. For example, lipids which can be used along with the peptides of the present invention may be exemplified by dipalmitoylphosphatidylcholine (DPPC), palmitoyloleylphosphatidylglycerol (POPG), phosphatidylglycerol (PG), C18 saturated fatty acids, C16 unsaturated fatty acids and C18 unsaturated fatty acids.

According to the administration route, the composition of the present invention may be formulated into various dosage forms comprising pharmaceutically acceptable carriers. Appropriate dosage forms are well known in the art, and may comprise typical additives which help the peptides penetrate or move into the cell.

The composition comprising the peptides as active ingredients in accordance with the present invention may be used in general medicinal preparations. Non-oral dosage forms may be sterile aqueous solutions, non-aqueous solutions, suspensions, emulsions, or freeze-dried preparations. Examples of oral dosage forms suitable for the composition of the present invention include tablets, troches, capsules, elixirs, suspensions, syrups, or wafers. Injections may be prepared into, for example, single-dose ampules or multi-dose forms.

Also, the pharmaceutical composition of the present invention may comprise pharmaceutically acceptable excipients. For example, excipients suitable for use in oral administration include binders, lubricants, disintegrants, expedients, solubilizers, dispersants, stabilizers, suspending agents, dyes, and/or flavors. Injections may contain additives, such as buffers, preservatives, pain-relieving agents, solubilizers, isotonics, and stabilizers, in combination. For topical administration, bases, expedients, lubricants and preservatives may be used.

Optionally, the composition of the present invention may comprise nucleic acid sequences encoding the peptides of the present invention, which can act as templates for expressing the peptides within cells.

In accordance with a further aspect, the present invention pertains to a method for inhibiting transglutaminase, comprising the administration of one or more of the peptides or the composition.

Preferably, a method, featuring the administration of one or a composition of the peptides of the present invention so as to inhibit transglutaminase-mediated I-KκBα polymerization, is provided for preventing or treating immune diseases.

In an embodiment of the present invention, the method for inhibiting transglutaminase is effected by administering one or more of the peptides or the composition of the present invention into patients via suitable routes. The administration may use intraperitoneal, intravenous, intramuscular, subcutaneous, intracutaneous, oral, topical, intranasal, intrapulmonary, or rectal routes, but is not limited thereto. For oral administration, the peptides may be preferably coated with a suitable substance or formulated into preparations so as not to be digested or dissolved within the stomach. Also, the pharmaceutical composition of the present invention may be administered with the aid of a means for delivering the active ingredient into target cells. Preferable is intravenous injection, subcutaneous injection, intracutaneous injection, or instillation. Injection preparations may be based on aqueous solvents, such as physiological saline or Ringer's solution, or non-aqueous solutions, such as vegetable oils, higher fatty acid esters (e.g., ethyl oleate, etc.), and alcohols (e.g., ethanol, benzyl alcohol, propylene glycol or glycerin) and may comprise pharmaceutically acceptable vehicles, such as antiseptic stabilizers (e.g., ascorbic acid, sodium hydrogen sulfite, sodium pyrosulfite, BHA, tocopherol, EDTA, etc.), emulsifiers, pH-adjusting buffers, and/or anti-microbial preservatives (e.g., phenylmercuric nitrate, thimerosal, benzalkonium chloride, phenol, cresol, benzyl alcohol, etc.).

In a preferable embodiment of the present invention, the method for inhibiting transglutaminase is effected by administering the peptide or the composition of the present invention in a therapeutically effective amount. The therapeutically effective amount for patients may vary depending on various factors well known in the medical art, including the kind of disease, the patient's condition, such as age, body weight, state of health, sex, drug sensitivity, etc., the route, frequency, and time of administration, the time period of therapy, formulations, other drugs used therewith, etc.

In accordance with still a further aspect, the present invention pertains to a method for preparing mutant derivatives of the peptides, which still inhibit transglutaminase-mediated I-κBα polymerization, comprising substituting, deleting or inserting one or more amino acid residues of the amino acid sequences for the peptides.

In an embodiment of the present invention, I-κBα-derived transglutaminase mutants are found to have inhibitory activity against transglutaminase.

A better understanding of the present invention may be obtained in light of the following examples which are set forth to illustrate, but are not to be construed to limit the present invention.

EXAMPLE 1:

Cross-Linking Site of I-κBα by Transglutaminase

I-κBα Polymerization by Transglutaminase

Figure 3:
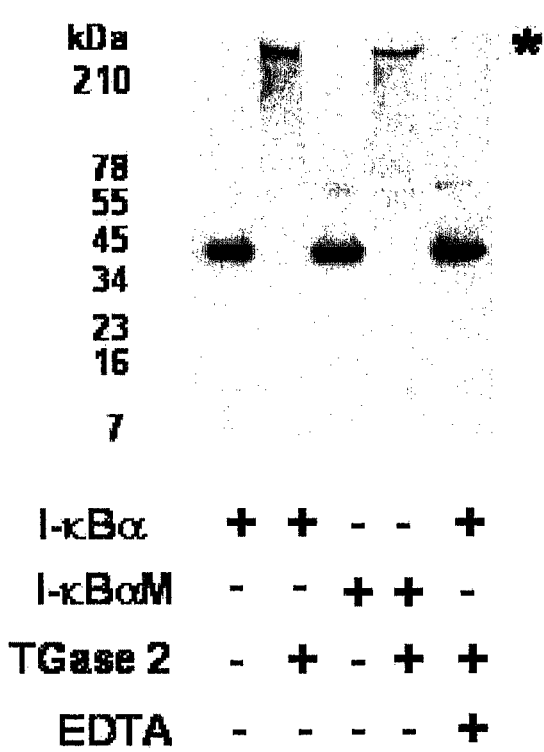
FIG. 3 shows the polymerization of separate I-kBa by transglutaminase as identified on 4-12% NuPAGE (Invitrogen)

Human I-κBα was expressed in *E. coli* BL21(DE3) in a large amount and purified before use. *E. coli* BL21 carrying the pET-30 EK/LIC vector to which the human I-κBα gene was sub-cloned was cultured in an LB broth at 37° C. in the presence of 100 ppm of kanamycin. When the broth reached an OD of 0.2-0.3, 0.2-1.0 mM of IPTG (Isopropyl-β-D-Thiogalactopyranoside) was added, followed by the induction of expression of I-κBα for 3-12 hrs. After centrifugation, the cell pellet was subjected to sonication, and, thanks to the N-terminal His-tag, I-κBα was primarily separated using Ni-NTA resin. The N-terminal His-tag was completely separated by digestion with enterokinase and re-binding to Ni-NTA resin, so as to afford an intact I-κBα. For in vitro polymerization, 10 pg of the purified I-κBα was incubated with 1 mU transglutaminase (guinea pig liver, Sigma) in a reaction mixture containing 50 mM Tris-HCl pH 7.5 and 10 mM $CaCl_2$. Polymerization was analyzed using 4-12% NUPAGE gel electrophoresis (Invitrogen) (FIG. 3). I-κBα polymers thus formed were separated using a centrifugal filter device (Centricon, M.W. cut-off 100 kDa, Millipore). As seen in FIG. 3, both the intact I-κBα and the mutant I-κBα, the phosphorylation sites of which were modified, were polymerized to high-molecular weight polymers, by transglutaminase. As a Ca-dependent enzyme, the transglutaminase was inhibited in the presence of EDTA.

Proteolysis of I-κBα Polymer

For denaturation, a purified I-κBα polymer (10 μg) was incubated overnight at 55° C. in 4 M urea containing 10 mM dithiolthreitol, and the concentration of urea was diluted to 1 M using 100 mM $NH_4HCO_3$. The polymer was digested overnight at 37° C. with trypsin (Promega) or endoproteinase Glu-C (V8, Roche).

MALDI-TOF MS Analysis

The mass of the digested peptides was determined using a MALDI-TOF mass spectrometer (4700 Proteomics Analyzer, Applied Biosystems) (FIGS. 4 and 5). Samples were desalted using a Zip-Tips C18 (Millipore), eluted in a matrix solution (CHCA in 1:1 v/v 0.1% TFA/CAN) directly onto the mass analysis target and dried. Analyses were performed in positive ion reflectron mode, and the measured mass spectra were calibrated at 50 ppm tolerance using standard samples from 4700 Cal Mix (Applied Biosystems). The standard samples used were as follows; des-Argl-bradykinin (Mr 904.4681), angiotensin 1 (Mr 1296.6853), $Glu^1$-fibrinopeptide B (Mr 1570.6774), ACTH 1-17 clip (Mr 2093.0867), ACTH 18-39 clip(Mr 2465.1989), and ACTH 7-38 clip (Mr 3657.9294). A Data Explorer software (Applied Biosystems) was used for data processing. Following the removal of peaks corresponding to keratins and proteases themselves, measured peaks were matched with theoretically possible peptide peaks. For this, A Paws program (Genomic Solutions) was used at 100 ppm tolerance.

EXAMPLE 2:

Protein Assay with Glu-C Digests of I-κBα Polymer

Competition Assay

I-κBα (2 μg) was incubated with 0.5 mU TGase in a reaction buffer containing 50 mM Tris pH 7.5 and 10 mM $CaCl_2$, with or without the peptides (2 nmol) of Table 1, so as to observe the cross-linking of I-κBα. The peptides of Table 1 were synthesized in Peptron Inc. After incubation for 10 min at 37° C., the reactants were separated by SDS-PAGE and visualized by Coomassie staining. Bands were measured for intensity using Adobe Photoshop software (FIGS. 7 and 8).

As seen in FIGS. 7 and 8, peptides containing particularly the N-terminal glutamine cluster (Q266-Q268), lysine 177, or glutamine 313 are excellent competitors, and lysine residues 21 and 22 competitively inhibit the enzyme.

TABLE 1

Synthetic Peptides for Competition Assay

| Name | Amino Acid Sequence | | M.W. (Mo) |
|---|---|---|---|
| PK-1 | RDGL<u>KK</u>ERLL | 17-26 | 1226.7456 |
| PK-2 | IHEE<u>K</u>ALTM | 83-91 | 1070.5430 |
| PK-3 | HSIL<u>K</u>ATNY | 173-181 | 1045.5556 |
| PK-4 | IL<u>K</u>AT | 175-179 | 544.3584 |
| PQ-1 | GVLT<u>Q</u>SCTT | 161-169 | 908.4273 |
| PQ-2 | ENL<u>Q</u>MLP | 275-281 | 843.4160 |
| PQ-3 | VFGG<u>Q</u>RLTL | 309-317 | 989.5658 |
| PQ-4 | TRI<u>QQQ</u>LG<u>Q</u>LTL | 263-274 | 1397.7990 |
| PQ-5 | RI<u>QQQ</u>LG | 264-270 | 841.4770 |
| PQ-6 | RI<u>Q</u>EELG | | 843.4450 |
| PQ-7 | RIE<u>Q</u>ELG | | 843.4450 |
| PQ-8 | RIEE<u>Q</u>LG | | 843.4450 |
| PQ-9 | LG<u>Q</u>LT | 269-273 | 530.3064 |

Industrial Applicability

Acting as transglutaminase inhibitors, as described hitherto, the peptides or a pharmaceutical composition comprising one of them in accordance with the present invention are very useful in the prevention and treatment of diseases caused by the aberrant activation of transglutaminase, particularly in the prevention and treatment of inflammatory diseases and cancers.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced other than as specifically described.

The invention claimed is:

1. A method for inhibiting transglutaminase, comprising administering to a subject a transglutaminase inhibitor that inhibits transglutaminase-mediated I-κBα polymerization in said subject, wherein the transglutaminate inhibitor comprises at least one peptide selected from the group consisting of SEQ ID NOs: 2 to 14.

2. The method according to claim 1, wherein the subject is suffering from a disease caused by the increased activation of transglutaminase and the disease caused by the increased activation of transglutaminase is an inflammatory disease or a cancer and wherein the inhibiting treats the disease.

* * * * *